(12) United States Patent
Hetzel et al.

(10) Patent No.: US 11,224,687 B2
(45) Date of Patent: Jan. 18, 2022

(54) MEDICAL INSTRUMENT FOR THE TARGETED INTRODUCTION OF A SUBSTANCE INTO A BODY CAVITY, AND TOOL THEREFOR

(71) Applicant: Prof. Reymond & Hetzel GbR, Villingendorf (DE)

(72) Inventors: Alexander Hetzel, Villingendorf (DE); Marc Reymond, Tübingen (DE)

(73) Assignee: Prof. Reymond & Hetzel GbR, Villingendorf (DE)

( * ) Notice: Subject to any disclaimer, the term of this patent is extended or adjusted under 35 U.S.C. 154(b) by 0 days.

(21) Appl. No.: 17/272,701

(22) PCT Filed: Aug. 29, 2019

(86) PCT No.: PCT/EP2019/000248
§ 371 (c)(1),
(2) Date: Mar. 2, 2021

(87) PCT Pub. No.: WO2020/048626
PCT Pub. Date: Mar. 12, 2020

(65) Prior Publication Data
US 2021/0308362 A1    Oct. 7, 2021

(51) Int. Cl.
*A61M 3/02* (2006.01)
*A61M 31/00* (2006.01)

(52) U.S. Cl.
CPC ........ *A61M 3/0279* (2013.01); *A61M 3/0254* (2013.01); *A61M 31/00* (2013.01); *A61M 2205/103* (2013.01)

(58) Field of Classification Search
CPC .. A61M 3/0279; A61M 3/0254; A61M 31/00; A61M 2205/103; A61M 2025/0019; A61M 35/20; A61M 1/842; A61M 25/0082; A61M 25/0068; A61M 25/007; A61B 2217/007; A61B 2218/001; A61B 2218/002; A61B 2218/003
See application file for complete search history.

(56) References Cited

U.S. PATENT DOCUMENTS

| | | | | |
|---|---|---|---|---|
| 3,120,346 A | * | 2/1964 | Willhoite | B05B 13/0636 239/214.13 |
| 3,601,316 A | * | 8/1971 | Murray | B05B 3/0427 239/73 |
| 3,848,603 A | * | 11/1974 | Throner | A61L 29/16 604/540 |

(Continued)

FOREIGN PATENT DOCUMENTS

| | | |
|---|---|---|
| CA | 2 360 411 | 7/2000 |
| DE | 73 09 776 | 8/1973 |

(Continued)

*Primary Examiner* — Nilay J Shah
(74) *Attorney, Agent, or Firm* — Gudrun E. Huckett

(57) ABSTRACT

The present invention relates to a medical instrument for the targeted introduction of a substance into a body cavity and to a tool (1) therefor. According to the invention, the tool (1) has a shaft (2) with a lumen (6), on the distal end (1") of which is situated a nozzle head (3) with at least two nozzles (4), wherein the nozzles (4) are spaced from each other at an angle of less than 180° and equally relative to a centre axis (M) of the shaft (2).

6 Claims, 5 Drawing Sheets

(56) References Cited

U.S. PATENT DOCUMENTS

| | | | |
|---|---|---|---|
| 4,631,052 A * | 12/1986 | Kensey | A61B 17/320758 604/22 |
| 4,784,638 A * | 11/1988 | Ghajar | A61M 25/0015 138/103 |
| 4,950,238 A * | 8/1990 | Sullivan | A61B 17/32037 134/167 C |
| 5,273,526 A * | 12/1993 | Dance | A61B 17/22 604/35 |
| 5,800,407 A * | 9/1998 | Eldor | A61M 25/007 604/264 |
| 5,964,414 A * | 10/1999 | Hardy | B05B 3/005 239/252 |
| 6,319,248 B1 | 11/2001 | Nahon | |
| 8,517,999 B2 * | 8/2013 | Pappone | A61M 25/1011 604/264 |
| 2002/0151873 A1 | 10/2002 | Moore | |
| 2003/0032859 A1 * | 2/2003 | Belson | A61B 1/00078 600/114 |
| 2009/0199848 A1 | 8/2009 | Sharratt | |
| 2013/0150805 A1 * | 6/2013 | Boomsma | A61B 18/1492 604/246 |
| 2014/0142495 A1 | 5/2014 | Hetzel et al. | |
| 2019/0307971 A1 * | 10/2019 | Levy | A61M 25/007 |

FOREIGN PATENT DOCUMENTS

| | | |
|---|---|---|
| DE | 33 20 076 | 12/1984 |
| DE | 20 2009 003 255 | 6/2009 |
| JP | S58-28599 | 6/1983 |
| JP | H05-168714 | 7/1993 |
| JP | 3293458 | 9/1997 |
| JP | 2001 104490 | 4/2001 |
| JP | 2001104489 | 4/2001 |
| KR | 20070090734 A * | 9/2007 |
| RU | 2198740 | 2/2004 |
| WO | 2012/163346 | 12/2012 |
| WO | 2013/063404 | 5/2013 |

\* cited by examiner

A - A

MEDICAL INSTRUMENT FOR THE TARGETED INTRODUCTION OF A SUBSTANCE INTO A BODY CAVITY, AND TOOL THEREFOR

BACKGROUND OF THE INVENTION

The invention concerns a medical instrument for targeted introduction of a substance into a body cavity, and a tool therefor.

From the prior art, in general connecting possibilities such as a Luer lock connector for fixed, detachable connections of tools and fluid conduits for medical applications are known, as in DE 20 2009 003 255 U1, for example.

Moreover, medical instruments are known in which a fluid is conducted. DE 73 09 776 U discloses a catheter that, at its distal end, comprises a head at which uniformly distributed openings are present from which a fluid can exit in order to position the catheter by repulsion in a targeted fashion.

DE 33 20 076 A1 discloses a nozzle member with a plurality of radially arranged nozzles for a medical instrument that is present in a shaft, is rotatably supported, and fixedly connected to a fluid-conducting hose. The rotational movement results from the repulsion of the fluid exiting from the nozzles and is transmittable to a shaft.

Also, tools for medical instruments are known which are designed for introducing substances, in particular therapeutic substances, into a body cavity.

WO 2012/163 346 A1 describes a trocar system with a tool that comprises a nozzle at its distal end, wherein the distal end can project into a body cavity. By means of this nozzle, a therapeutic substance can be sprayed in a pneumoperitoneum, for example. The spray direction of this nozzle is however directed only in one direction so that the substance cannot be sprayed uniformly within the abdomen.

Based on this prior art, it is object of the present invention to provide an improved tool for a medical instrument for targeted introduction of a substance into a body cavity that enables a uniform spraying of the respective substance in the body cavity.

SUMMARY OF THE INVENTION

This object is solved by a tool comprising a shaft with a lumen having at its distal end a nozzle head with at least two nozzles, wherein the nozzles are at an angle of less than 180° in relation to a center axis of the shaft and are uniformly spaced apart from each other.

The further object of providing a medical instrument, which is of a simple configuration and is cost-efficient, is solved by the instrument provided with a trocar, a fluid source as well as a tool that is connectable detachably to a handle and in fluid communication to the fluid source, characterized in that the tool is a tool according to the invention as claimed.

Further embodiments of the tool and of the medical instrument are disclosed in the dependent claims.

A first embodiment of the tool relates to a tool for a medical instrument for targeted introduction of a substance into a body cavity. This can be understood as any type of body cavity, preferred use can be in a pneumoperitoneum. As a substance, any fluid therapeutic substance, such as a medicament, medicament in solution or even a simple flushing solution is conceivable; it itself must sprayable or sprayable in a suitable solution.

According to the invention, the tool comprises a shaft with a lumen wherein, at the distal end of the shaft, a nozzle head with at least two nozzles is arranged. In this context, the nozzles, in relation to a center axis of the shaft, are at an angle of less than 180° and are uniformly spaced apart from each other. Advantageously, the nozzles are distributed uniformly at the nozzle head and form a symmetric arrangement in relation to the center axis of the shaft or of the tool.

In a further embodiment of the tool, the nozzles can have nozzle openings which are connected by a distributor cone to a bore and a lumen of the shaft. The lumen is located within the shaft and is formed by its inner bore that serves as a fluid access to the nozzles. By means of the distributor cone, the nozzles are supplied uniformly with the fluid substance. The bore can be designed as a central bore but also off-center.

Moreover, the tool can provide that the nozzle head has three nozzles. In case of three nozzles, their fluid axes are positioned at an angle $\alpha$ in a range of 90° to 180°, preferably of 100° to 140°, particularly preferred 120°, relative to each other and in relation to the tool center axis, respectively. This angle is moreover also formed between the individual nozzles so that in the preferred case between the center axis of all three nozzles and a virtual center point of the nozzle head (originating at the center axis of the tool), the same angle $\alpha$=120° is present. In a further embodiment of the tool, two to ten nozzles can be arranged in a circular arrangement, as needed, on different axes. Preferably, the angle $\alpha$ is =360 degrees/number of nozzles. This symmetry produces the greatest possible distance between the nozzles and ensures, spatially considered, a good and uniform distribution of the sprayed substance.

In a further embodiment, the nozzle head can be supported rotatably in the shaft. For this purpose, an end face of the distal end of the shaft can be configured in correspondence to a shape of the nozzle head. In order to be rotatable, the nozzle head is of rotational symmetry relative to the center axis of the shaft or of the tool. In a preferred variant, the nozzle head can be round, substantially spherical. However, it can also be cylindrical as an alternative. Other shapes are also possible. In this context, the end face of the shaft (viewed in a longitudinal section) can be embodied flat, rounded, part-spherical, conical or in another shape.

The nozzle head can be produced by a generative manufacturing process and can be matched with precise fit to the shaft. In a preferred embodiment, an outer diameter of the shaft is approximately 10 mm. This dimension fits in existing trocar systems wherein also diameters in a range of 1 mm to 30 mm are possible.

In a further embodiment of the tool, the nozzle head can comprise a cylindrical body which is received in the lumen of the shaft. The nozzle body can have an annular groove in which, for example, an annular sliding seal is received. The nozzle body can thus be rotatably supported in the lumen without leaking. In a further embodiment, the nozzle body comprises an impeller with a plurality of vanes in a proximal section and a bearing ring, that serves to secure the nozzle head in the shaft of the tool, in a distal section which adjoins the nozzle head. This nozzle body is inserted into the shaft in such a way that the impeller (or its position) in a mounting arrangement of the tool corresponds with a through opening with two lumina in the shaft through which the fluid can flow.

As the fluid impinges on the vanes of the impeller, the nozzle body is caused to rotate. The entire fluid can be guided through the lumina, across the impeller and to the central bore, and subsequently the nozzle of the tool.

Between the impeller and the bearing ring, a cylindrical sliding surface is provided on which the components can glide with low friction. The shaft comprises a cutout corresponding to the nozzle body in order to accommodate in particular the bearing ring. The head can thus be caused to rotate easily and held securely in the tool at the same time.

In order to be able to connect the tool with a trocar of a trocar system, a hand piece or a handle or other existing instruments and to be able to connect a fluid source, the shaft can comprise at its proximal end a connector for fluid communication of the lumen with a fluid source, wherein the connector is a Luer lock connector. However, other connections are possible also.

The invention relates moreover to a medical instrument for introducing fluids into a body cavity. The instrument can comprise a trocar, a fluid source as well as a tool wherein the tool can be detachably connected to the trocar and to the fluid source in fluid communication. The tool according to the invention is employed.

According to the invention, the tool, when it is used with the trocar within a trocar system, is connected to the fluid source by means of a flexible fluid conduit, wherein the fluid source can be detachably connected to the tool and the tool can be inserted into the trocar of the medical instrument. Also, a handle can be provided into which the tool can be inserted. By actuation of appropriate actuation elements at the handle or the trocar, the tool can be supplied with the substance to be sprayed in that a fluid communication connection between the fluid source and the tool is produced. The fluid substance passes through the lumen to the nozzle body, is guided through the central bore of the nozzle body to the distributor cone and from there via the supply conduits to the nozzle openings of the nozzles. The substance exits through the nozzle openings and is sprayed. Due to the uniform supply of the nozzles from the distributor cone and the arrangement according to the invention of the nozzles at the nozzle head, the nozzle head experiences a torque at a liquid pressure in a range of 1 bar to 100 bar and begins to rotate when it is supplied with the fluid substance. The result is a uniform distribution of the substance in the respective body cavity; a purely pointed spray is prevented. It is not necessary for the entire tool to rotate; instead, only the head rotates on its own.

Further embodiments of the tool and of the medical instrument as well as some of the advantages which are associated with this and further embodiments will become apparent and better understood due to the following detailed description with reference to the accompanying drawings. The Figures are only a schematic illustration of an embodiment of the invention.

BRIEF DESCRIPTION OF THE DRAWINGS

It is shown in.

DESCRIPTION OF PREFERRED EMBODIMENTS

Figure 1:
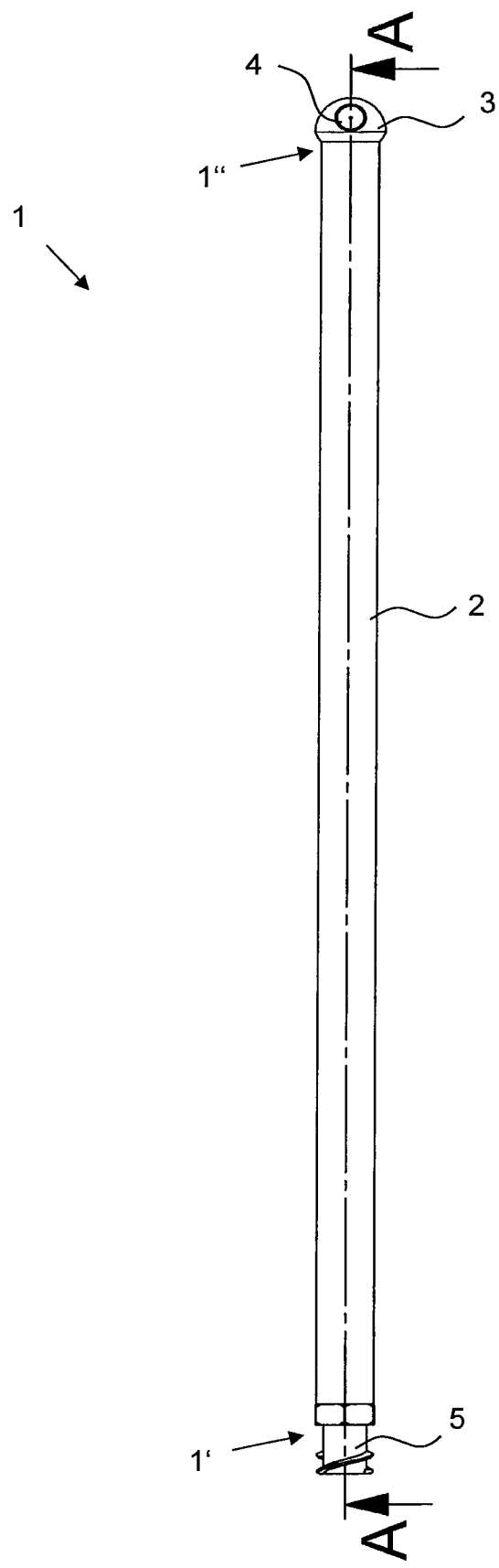
FIG. 1 a schematic side view of the tool according to the invention.
Figure 2:
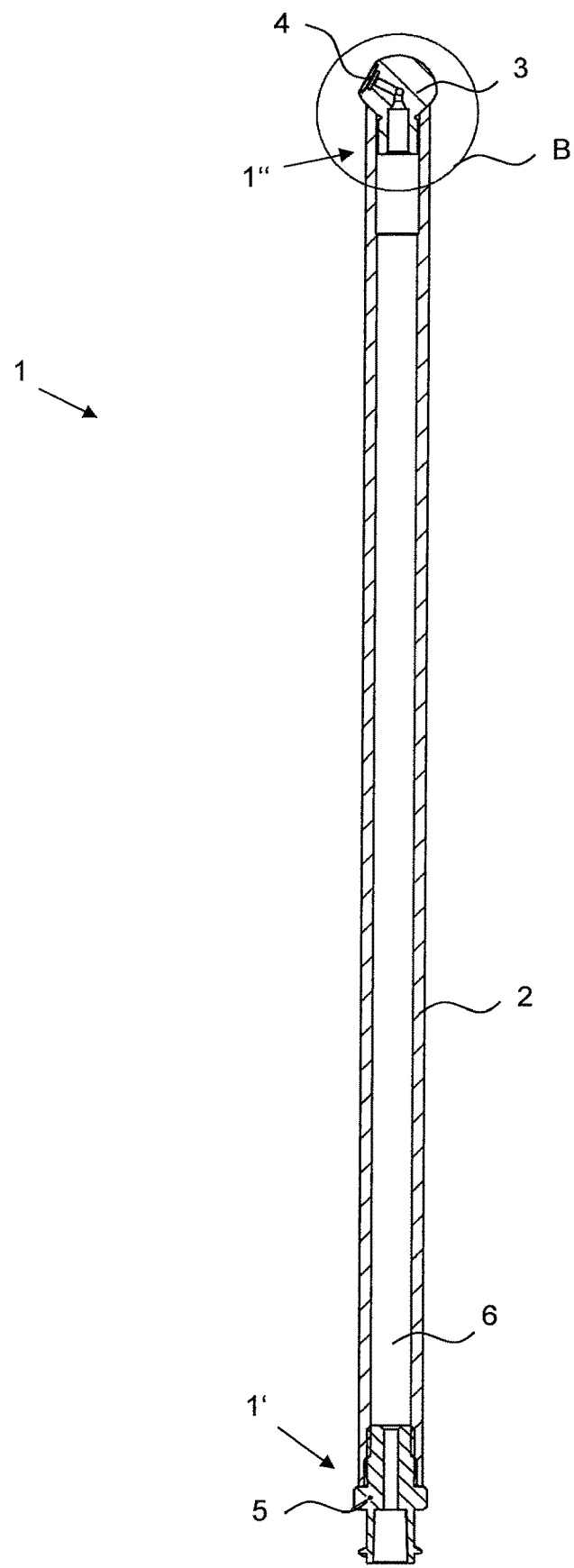
FIG. 2 a longitudinal section view A-A of the tool.
Figure 3:
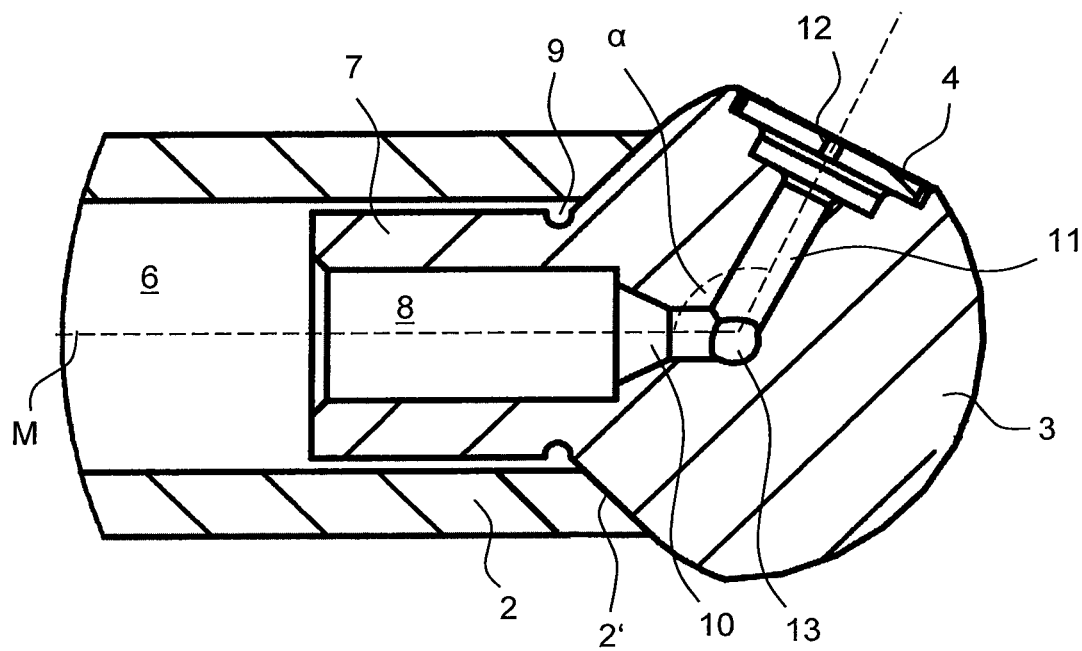
FIG. 3 a detail view B of the nozzle head in longitudinal section.

The device according to the invention relates to a medical instrument that comprises a tool 1 which, according to FIG. 1, has a shaft 2 with a proximal end 1' and a distal end 1". FIGS. 1 to 3 show the tool 1 in individual details. At the proximal end 1', there is a connector, a so-called Luer lock 5, to which different hoses or liquid supplies can be connected. The Luer lock 5 is in fluid communication with the lumen 6 (see section view A-A in FIG. 2). The shaft 2 is elongate and tubular and has a diameter of approximately 10 mm in a preferred embodiment. Diameters in a range of 1 mm to 30 mm are possible.

At its distal end 1", the shaft 2 comprises moreover a nozzle head 3 with a plurality of nozzles 4. In FIG. 3, a detail view B of the nozzle head 3 is illustrated. The nozzle head 3 comprises a nozzle body 7 with a cavity as well as an annular groove 9 which is arranged shortly below a spherical thickened portion of the nozzle head 3. The cavity is embodied as a bore 8 or central bore and is connected in fluid communication with a distributor cone 10. A supply channel 11 extends at an angle α of approximately 120° in relation to a center axis M of the bore 8 away from the bore 8 and connects it in fluid communication with a nozzle opening 12. Between distributor cone 10 and supply channel 11, a spherical collecting cavity 13 is provided which forms also the center point of the nozzle head 3. The bore 8 is connected in fluid communication with the lumen 6 of the shaft 2. The center axis M of the bore 8 as a central bore corresponds in this context to the center axis M of the shaft 2 and therefore also of the tool 1.

Figure 5:
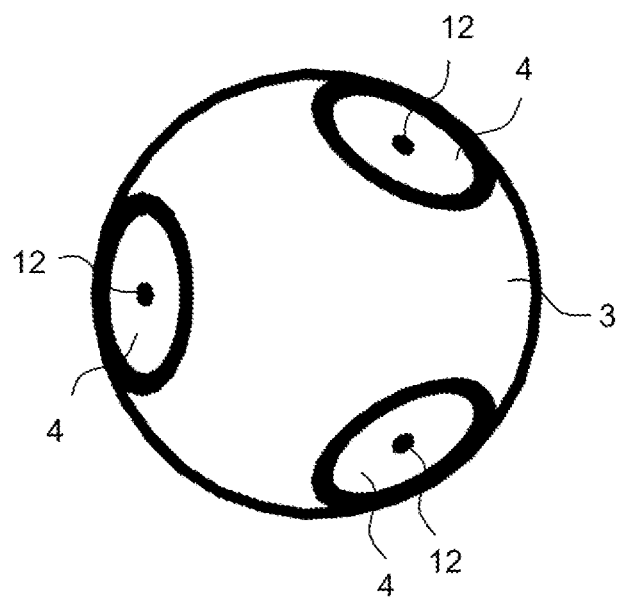
FIG. 5 a schematic plan view of the distal end of the nozzle head.

The head 3 is substantially spherically designed and comprises, as shown in FIG. 5, a total of three nozzles 4. The nozzles 4 are uniformly distributed about the spherical body 3 and are positioned respectively at an angle of 120° relative to the center point of the head 3. The head of the tool can comprise arbitrarily two to ten nozzles which are arranged in a circular arrangement relative to each other, as needed on different axes.

In this way and in particular due to the shape illustrated in FIG. 5, a particularly uniform distribution of the fluid sprayed through the nozzle 4 is achieved. The center point of the nozzle head 3 corresponds in this context to a spatial center of the collecting cavity 13.

Fluid that passes from the lumen 6 via the bore 8 into the distributor cone 10 is guided from there to the downstream reduced cross section and guided from the collecting cavity 13 to the individual supply channels 11 and then supplied to the respective nozzle opening 12.

Figure 4:
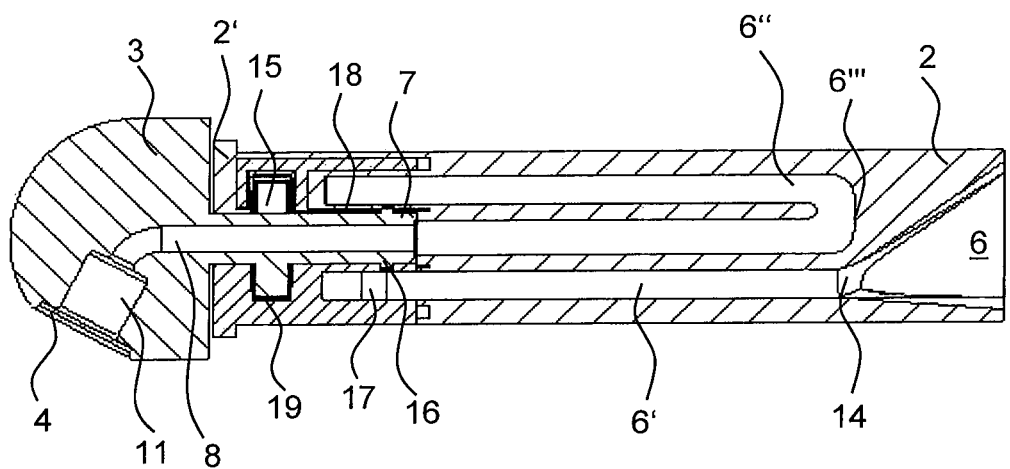
FIG. 4 a section view of a further embodiment of the nozzle head.

The head 3 is rotatable, as can be seen in FIGS. 3 and 4. An end face 2' of the distal end 1" of the shaft 2 is correspondingly designed thereto so that the nozzle head 3 is supported at the distal end 1" of the shaft 2. The end face 2' of the shaft 2 is conical in FIG. 3 and accommodates partially the head 3.

In FIG. 4, the head 3, at its side that is facing the distal end 1" and thus the end face 2', is embodied of a flat configuration so as to correspond to the end face 2' which is also flat here. So that the nozzle body 7 during use is not pushed out of the shaft 2, the nozzle body 7 and the shaft 2 have the following components: The lumen 6 of the shaft 2 tapers to the distal end 1" of the tool 1 and opens in a cone 14 that connects the lumen 6 to a lumen 6' whose diameter is strongly tapered in comparison to the lumen 6. The cone 14 in FIG. 4 is arranged in a lower third of the shaft 2 wherein the lumen 6' extends parallel to the center axis. The lumen 6' comprises in its distal end region a through opening 17 through which the fluid can be guided out of the lumen 6' to an impeller 16. The nozzle body 7 comprises a plurality of vanes which form the impeller 16. By means of the impeller 16, the fluid is guided into a further lumen 6" and through a bend 6''' into the bore 8 of the nozzle body 7. From here, the bore 8 extends into the supply channel 11 and to the nozzle 4. At the nozzle body 7, there is moreover a bearing ring 15 which is rotatably supported in the shaft body 2. For this purpose, in the shaft body 2 a corresponding circular cylindrical cutout 19 is formed as a receptacle. In this way, the nozzle body 7 is held in the shaft 2. Between bearing ring 15 and impeller 16, a sliding surface 18 is provided so that the nozzle body 7 can rotate with low friction in the shaft 2.

Figure 6:
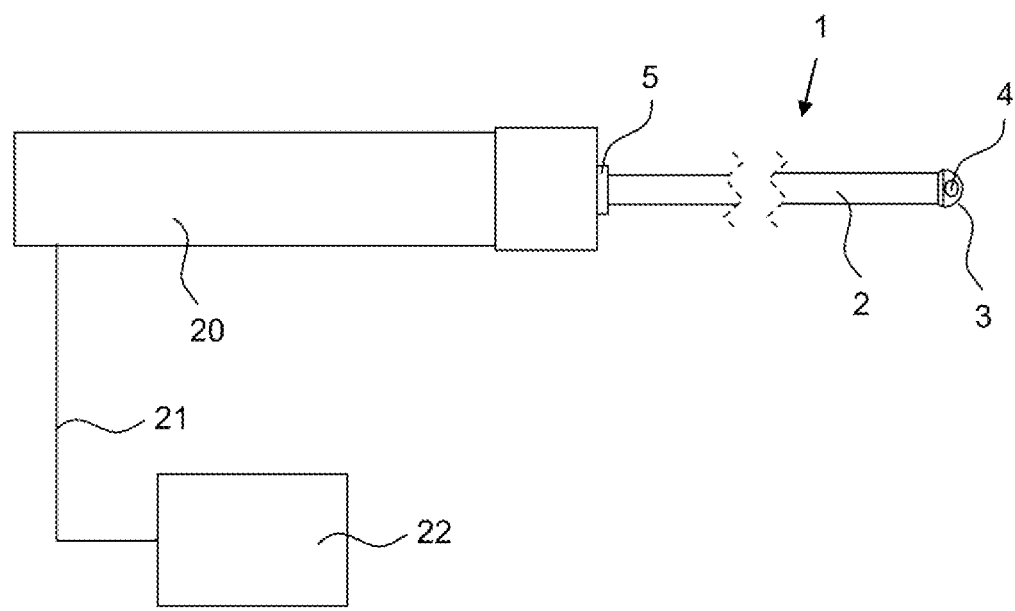
FIG. 6 a schematic view of a handle with inserted tool.
Figure 7:
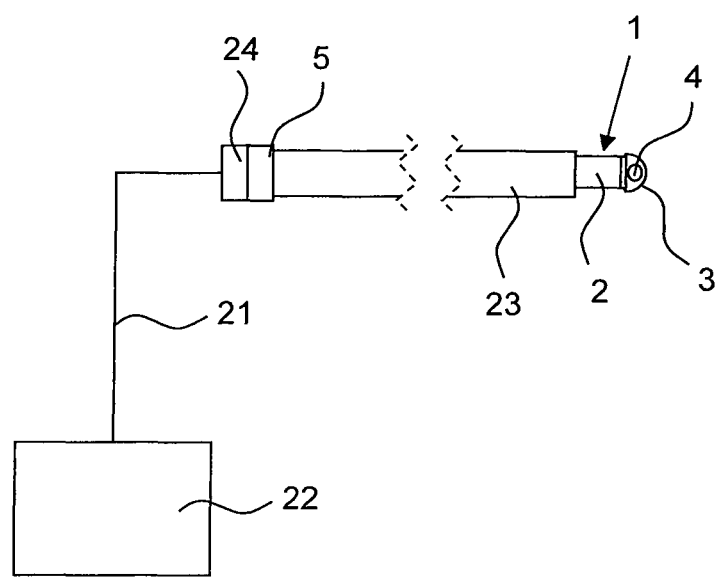
FIG. 7 a schematic view of a trocar with inserted tool.

The tool 1 can be connected by means of the Luer lock connector 5 to a handle 20 and a fluid source 22, as illustrated in FIG. 6. The fluid source 22 is connected by a fluid conduit 21 in fluid communication to the handle 20 and thus to the tool 1. Moreover, the tool 1 can also be used together with a trocar system in the context of minimal invasive surgery, as illustrated in FIG. 7. For this purpose, the tool 1 is inserted into a trocar 23. By means of a connectable fluid connector 24, the tool 1 can be connected via a fluid conduit 21 in fluid communication to the fluid source 22.

LIST OF REFERENCE CHARACTERS 1 tool
1' proximal end
1" distal end
2 shaft
2' end face
3 nozzle head
4 nozzle
5 Luer lock connector
6, 6', 6" lumen
6''' bend
7 nozzle body
8 bore
9 annular groove
10 distributor cone
11 supply channel
12 nozzle opening
13 collecting cavity
14 cone
15 bearing ring
16 impeller
17 through opening
18 sliding surface
19 cutout
20 handle
21 fluid conduit
22 fluid source
23 trocar
24 fluid connector
A-A a longitudinal section
B head in detail
M center axis

What is claimed is:

1. A tool (1) for a medical instrument for targeted introduction of a substance into a body cavity,
   wherein the tool (1) comprises a shaft (2) with a lumen (6), the shaft (2) having at a distal end (1") thereof a nozzle head (3) with at least two nozzles (4), wherein the nozzles (4) are positioned at an angle of less than 180° ($\alpha$) in relation to a center axis (M) of the shaft (2) and are uniformly spaced apart from each other and comprise nozzle openings (12),
   wherein the nozzle openings (12) are connected by a distributor cone (10) to a bore (8) and to the lumen (6), and
   wherein the nozzle head (3) is rotatably supported in the shaft (2) and experiences a torque when the nozzles (4) are supplied with the substance;
   wherein the nozzle head (3) comprises a cylindrical nozzle body (7) which is received in the lumen (6) of the shaft (2), and wherein the nozzle body (7) comprises an annular groove (9) in which an annular sliding seal can be received;
   wherein the nozzle body (7) comprises in a proximal section an impeller (16) with a plurality of vanes and a bearing ring (15) in a distal section which adjoins the nozzle head (3), and
   wherein the shaft (2) comprises two lumina (6', 6") that are connected by a bend (6''') to each other and each comprise a through opening (17) which coincides with the position of the impeller (16) in a mounting arrangement of the tool (1).

2. The tool (1) according to claim 1, wherein the at least two nozzles (4) comprise three nozzles (4) which are positioned at an angle of 120° ($\alpha$) in relation to the center axis (M) of the shaft (2) and are uniformly spaced apart from each other.

3. The tool (1) according to claim 1, wherein an end face (2') of the distal end (1") of the shaft (2) is embodied so as to correspond to a shape of the nozzle head (3).

4. The tool (1) according to claim 1, wherein the shaft (2) at a proximal end (1') thereof comprises a connector (5) for fluidly connecting the lumen (6) to a fluid source (22), wherein the connector (5) is a Luer lock connector.

5. A medical instrument for introduction of fluids into a body cavity, the medical instrument comprising a trocar (23), a fluid source (22), and a tool that is connectable detachably to a handle (20) and in fluid communication to the fluid source (22), wherein the tool is a tool (1) according to claim 1.

6. The medical instrument according to claim 5, wherein the tool (1) is connected to the fluid source (22) by a flexible fluid conduit (21).

* * * * *